United States Patent
Sakata et al.

(10) Patent No.: US 6,548,045 B2
(45) Date of Patent: Apr. 15, 2003

(54) NITROIMIDAZOLE SUBSTITUTED PORPHYRIN COMPLEX

(75) Inventors: Isao Sakata, Okayama (JP); Susumu Nakajima, Asahikawa (JP); Yoshinori Nakae, Okayama (JP)

(73) Assignee: Photochemical Co., Ltd., Okayama (JP)

( * ) Notice: Subject to any disclaimer, the term of this patent is extended or adjusted under 35 U.S.C. 154(b) by 0 days.

(21) Appl. No.: 09/889,778

(22) PCT Filed: Nov. 29, 2000

(86) PCT No.: PCT/JP00/08385

§ 371 (c)(1),
(2), (4) Date: Jul. 20, 2001

(87) PCT Pub. No.: WO01/40233

PCT Pub. Date: Jul. 6, 2001

(65) Prior Publication Data

US 2002/0177704 A1 Nov. 28, 2002

(30) Foreign Application Priority Data

Nov. 30, 1999 (JP) ............................................ 11-339329
Nov. 30, 1999 (JP) ............................................ 11-339331

(51) Int. Cl.[7] ..................... C07D 487/22; A61K 31/555
(52) U.S. Cl. ..................... 424/9.362; 540/145; 514/185
(58) Field of Search ........................ 540/145; 514/185; 424/9.362

(56) References Cited

FOREIGN PATENT DOCUMENTS

| JP | 7330773 | 12/1995 |
|----|---------|---------|
| JP | 867682  | 3/1996  |

*Primary Examiner*—Mark L. Berch
*Assistant Examiner*—Kahsay Habte
(74) *Attorney, Agent, or Firm*—Crowell & Moring LLP

(57) ABSTRACT

The present invention provides the porphyrin compound having nitroimidazole in the molecule, which is used for diagnosis and/or treatment of cancer in magnetic resonance imaging (MRI) and/or radiotherapy as well as for DDS therapy. The porphyrin compound of the present invention shows no phototoxicity, and represented by the following formula:

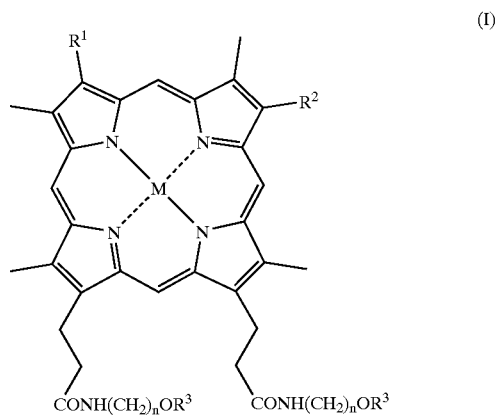

[wherein,
$R^1$ and $R^2$ are —CH=CH$_2$ or —CH(CH$_3$)—OH, —CH(CH$_3$)—O—(CH$_2$)$_n$—NH—$R^a$;
$R^3$ is hydrogen atom or —CO—(CH$_2$)$_m$—COOH; and
M is transition metal of Mn, Fe, Co or Cu],
(in which, $R^a$ is hydrogen atom or the group represented by the following formula:

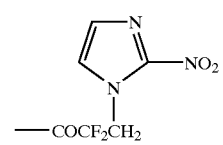

n and m are the integer 2 or 3),
or a pharmaceutically acceptable salt thereof.

20 Claims, 5 Drawing Sheets

US 6,548,045 B2

NITROIMIDAZOLE SUBSTITUTED PORPHYRIN COMPLEX

TECHNICAL FIELD

The present invention relates to a porphyrin metal complex having nitroimidazole group at the side chain thereof, and more specifically, to the porphyrin metal complex composed by connecting porphyrin metal complex which is used for missile therapy as drug delivery system (DDS), and nitroimidazole which is an effective radiosensitizer.

The present invention also relates to a contrast medium and a sensitizer used for diagnosis and/or treatment of cancer in magnetic resonance imaging (MRI) and/or radiotherapy, comprising of said porphyrin metal complex having nitroimidazole group at the side chain thereof, as an active ingredient.

Furthermore, the present invention relates to a porphyrin metal complex having a functional amino group capable of connecting with a physiologically active substance easily, for example anticancer agent, via an acidic functional group of said physiologically active substance such as carboxylic group, isothiocyanate group or azide group, at the side chain of the porphyrin complex, which is used for missile therapy.

BACKGROUND ART

As a new method of treatment for cancer, photodynamic fluorescent diagnosis and therapy (PDDT: Photodynamic Diagnosis and Therapy) has been performed. It is a method in which a certain type of porphyrin derivatives is administered to a subject by, for example, intravenous injection to retain the porphyrin derivative in the target cancerous tissues in the subject, followed by laser irradiation to fluorescent diagnose the cancerous tissues and cause selective destruction of said cancerous tissues. The therapy utilizes the two properties of a porphyrin derivative, i.e., longer retention time in cancerous tissues than normal tissues and photosensitivity of the porphyrin derivative.

For the past fifteen years, about 5,000 patients were treated of the malignant tumor by PDDT in the world, and PDDT has been fixed to be one of the methods for the treatment of caner. Many types of cancer are reported to be effectively treated by PDDT such as a cerebral tumor, a retina cancer, a cutaneous cancer, a cancer of the esophagus, sublimes vesical cancer and primary stage of lung cancer. Recently, PDDT has also been applied for fluorescent diagnosis of an endoscopy.

More recently, development of the treatment for cancer by DDS method applying the selective accumulability of porphyrin compound used in PDDT is reported. That is, the anticancer agent is connected to a porphyrin compound and accumulated to the cancerous tissues selectivity, and then, the essentially anticancer action of the drug is exhibited against the cancerous tissues directly. This method is expected to be the effective DDS therapy for the treatment of cancer instead of monoclonal antibody therapy.

The present inventors have synthesized more than 1,000 porphyrin compounds in order to develop the effective porphyrin compounds, considering the specific properties of these compounds, such as affinities, fluorescent and cell killing effects against the cancerous tissues, and reported the correlation between these affinities to cancerous tissues and the chemical structures (*Modern Medicine,* 1993, July; Asahi News Paper Co.,). Among them, certain porphyrin compounds were proposed to be a diagnosis and therapeutic agent for the photodynamic fluorescent treatment, a contrast medium for treatment of cancer in magnetic resonance imaging and neutron capture therapeutic agent. However, these porphyrin compounds were not specifically developed for applying to DDS therapy, and therefore, DDS effects of these compounds were not sufficient.

It is necessary for the porphyrin compounds to be the carrier of DDS therapy to connect with the porphyrin compound by covalence bonding, and to have the high functions such as affinity, fluorescent and cell killing effect against cancerous tissues in order to accumulate a physiologically active substance such as anticancer agent to the target tissues selectively and effectively.

By the way, radiotherapy is confirmed to be one of cancer therapies together with surgical treatment and chemotherapy; however, there are many problems in radiotherapy. For example, tumor is composed of approximately 20% of anoxic tissues and these anoxic tissues exhibit the resistance against the radioactive rays two to three times stronger than the normal tissues. Therefore, the presence of these anoxic tissues in the cancerous tissues is the main factor to prevent the improvement of radiotherapy and recurrence of tumor.

Accordingly, there have been developed drugs selectively elevating the radio-affinity of the anoxic tissues in tumor, and nitroazole derivatives having large electron affinities were proposed. Among them, nitroimidazoles were proposed to be effective drugs for radiosensitizers due to their sensitivities against an anoxic tissues, rapid metabolite rate and wide safety margin. Therefore, various nitorimidazole derivatives such as misonidazole have been developed.

Misonidazole, one of the representative compounds of sensitizer for anoxic tissues, exhibits twice times more efficacies in animal experiment implanting tumor compared with absence of this compound; however, it is difficult to administer effective dosage of this compound due to its high neurotoxin and no efficacy is observed in the case of the human being [*Gan to Kagakuryoho* (*Tumor and Chemotherapy*); vol. 8, 1656 (1981)].

On the contrary, the compound having fluorine atom at the certain position is awaited to be a medicine due to its mimic effect, its inhibition effect for metabolite and its increasing liposolubility. Based on this theory, nitroimidazole compound having fluorine atom in the molecular has been developed (*Int. J. Radiation Oncology Biol. Phys.,* 16, 1045 (1989); *ibid.,* 20, 1249 (1991); Japanese Patent Application Laid-open 2-76861). This nitroimidazole compound having fluorine atom in the molecular, however, shows low radiosensitizer effect even though elevating its radiosentisitizing effect and decreasing neurotoxicity. In general, imidazole type drugs may distribute to the whole organs of the living body and not specifically distribute to the cancerous tissues. Therefore, this nitroimidazole compound having fluorine atom in the molecular has confirmed to be a drug having no selective accumulability to cancerous tissues.

The present inventors synthesized porphyrin compounds having an amino group in the molecular to achieve the selective accumulability to cancerous tissues. Further, they also synthesized porphyrin metal complexes connecting nitroimidazole using said porphyrin compounds, and proposed these porphyrin metal complexes as effective contrast medium for treatment of cancer in magnetic resonance imaging and radiosentisitizer of radiotherapy and PDDT therapy (Japanese Patent Application Laid-open No. 8-67682).

In the process for synthesizing the porphyrin metal complexes having nitroimidazole in the molecular, it is difficult to establish the practical production method because there is a problem in synthesize of carrier. That is, there are so many steps to obtain the porphyrin compounds having amino group in the molecular from protoporphyrin dimethyl ester as a starting compound. Furthermore, drastically hard conditions for oxidation and reduction processes have to be present in the synthetic route of the porphyrin compounds, and therefore, the yield of the compounds is low.

This compound has the functional amino group at the side chain thereof in which nitroimidozole type drug may connect with by covalent bond. Because amino group was closely located to the skeleton of porphyrin ring, it was influenced by π-electron of porpyhrin nucleus, and the amino group is not reactive. Add to above problems, decrease in the phtotoxicity of the compound is not sufficient.

The present inventors have investigated to obtain the porphyrin complex in which the complex functions well having good affinities, fluorescent and cell killing effects against cancerous tissues and applicable for DDS therapy without photo toxicity. As the results, they found out that the porphyrin derivative having amino group at the side chain thereof, which is obtained from protoporphyrin dimethyl ester by treating with HBr and condensed with one or two aminoalcohols having appropriate carbon atoms to introduce the functional amino group at the terminal of the side chain, is treated with metal such as manganese (Mn) to obtain porphyrin derivative without any phototoxicity, which is the specific toxicity of porphyrin derivatives.

Furthermore, the present inventors found out that porphyrin metal complex having nitroimidazole, which is more potential anticancer agent, at the side chain of the aforementioned porphyrin derivative via the functional amino group thereof, shows effective accumulability to cancerous tissues, and to be the sensitizer with contrast ability for radiotherapy in the MRI method.

Therefore, it is an object of the present invention to provide a porphyrin metal complex composed by connecting porphyrin metal complex, which is carrier for drug, and nitroimidazole which is an effective anticancer agent.

Furthermore, it is other object of the present invention to provide a contrast medium and a sensitizer used for diagnosis and/or treatment of cancer in magnetic resonance imaging (MRI) and/or radiotherapy, comprising said porphyrin metal complex having nitroimidazole at the side chain thereof, as an active ingredient.

It is still another object of the present invention to provide a porphyrin metal complex used for DDS therapy capable of connecting with a physiologically active substance easily as missile therapy.

DISCLOSURE OF THE INVENTION

To solve the above-mentioned objects, one aspect of the present invention provides a porphyrin metal complex represented by the following formula (I):

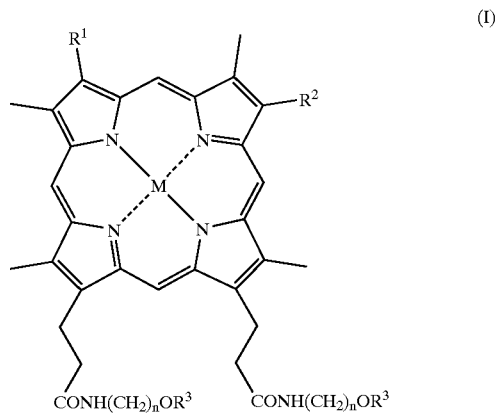

[wherein,
when one of $R^1$ and $R^2$ is —CH=$CH_2$ or —CH($CH_3$)—OH, the other is —CH($CH_3$)—O—($CH_2$)$_n$—NH—$R^a$; or both of $R^1$ and $R^2$ are —CH($CH_3$)—O—($CH_2$)$_n$—NH—$R^a$;
$R^3$ is hydrogen atom or —CO—($CH_2$)$_m$—COOH;
M is transition metal of Mn, Fe, Co or Cu],
in which, $R^a$ is hydrogen atom or the group represented by the following formula:

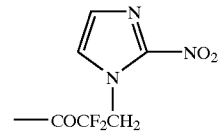

n and m are the integer 2 or 3,
or a pharmaceutically acceptable salt thereof.

As more specific embodiment of the present invention, it is provided a porphyrin metal complex represented by the above formula (I) used for DDS therapy capable of connecting with a physiologically active substance easily as missile therapy, wherein;

when one of $R^1$ and $R^2$ is —CH=$CH_2$ or —CH($CH_3$)—OH, the other is —CH($CH_3$)—O—($CH_2$)$_n$—$NH_2$; or both of $R^1$ and $R^2$ are —CH($CH_3$)—O—($CH_2$)$_n$—$NH_2$;
$R^3$ is hydrogen atom;
n is the integer 2 or 3;
M is transition metal of Mn, Fe, Co or Cu],
or a pharmaceutically acceptable salt thereof.

As more specific embodiment of the present invention, it is provided a porphyrin metal complex having nitorimidazole at the side chain thereof represented by the above formula (I), wherein;

when one of $R^1$ and $R^2$ is —CH=$CH_2$ or —CH($CH_3$)—OH, the other is —CH($CH_3$)—O—($CH_2$)$_n$—NH—$R^a$; or both of $R^1$ and $R^2$ are —CH($CH_3$)—O—($CH_2$)$_n$—NH—$R^a$;
$R^3$ is hydrogen atom or —CO—($CH_2$)$_m$—COOH;
M is transition metal of Mn, Fe, Co or Cu],
in which, $R^a$ is the group represented by the following formula:

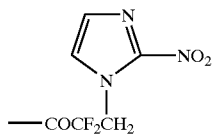

n and m are the integer 2 or 3, or a pharmaceutically acceptable salt thereof.

Another aspect of the present invention provides a sensitizer used for diagnosis and/or treatment of cancer in magnetic resonance imaging (MRI) and/or radiotherapy, comprising of said porphyrin metal complex having nitroimidazole at the side chain thereof, as active ingredient.

BEST MODE FOR CARRYING OUT THE INVENTION

Figure 1:
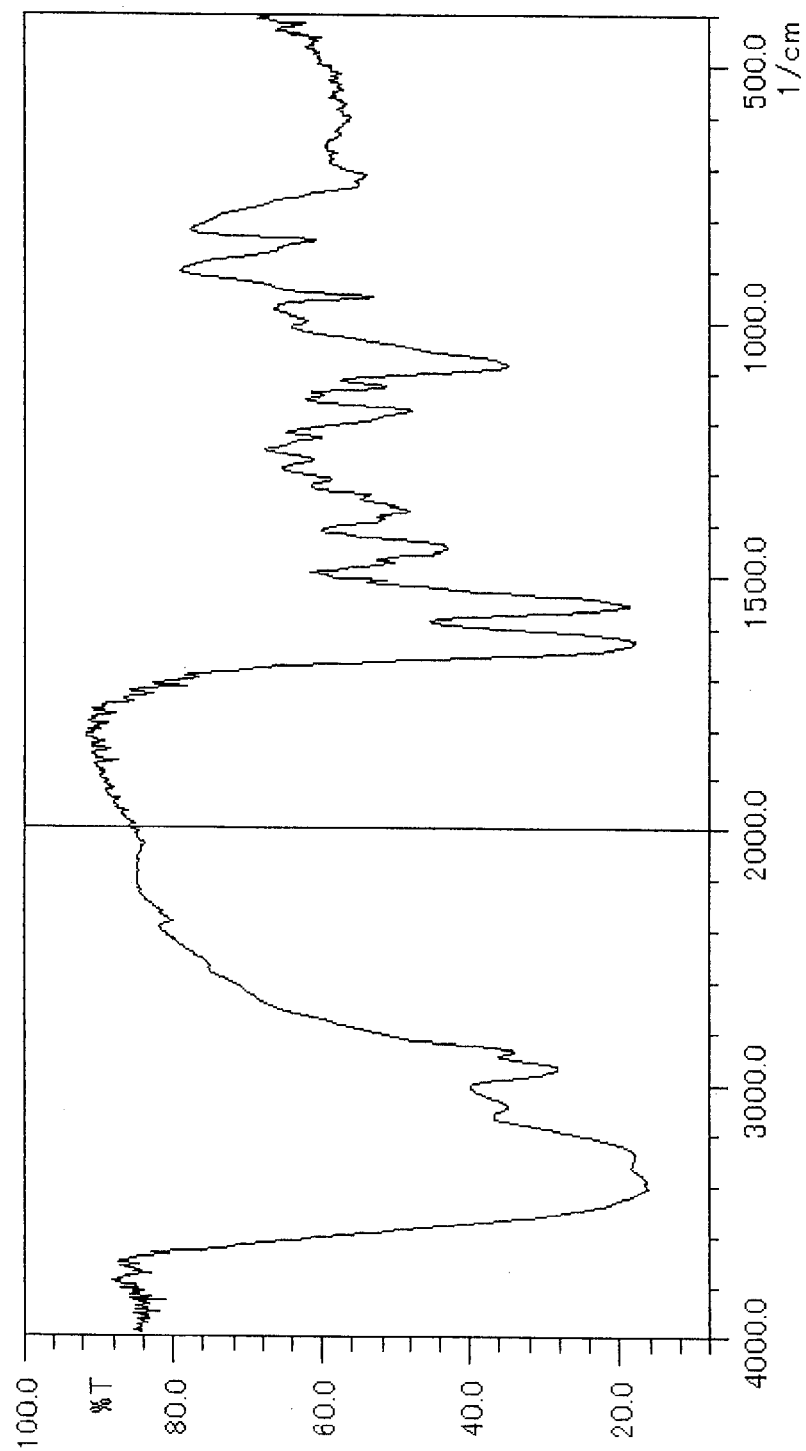
FIG. 1 shows an infrared absorption spectrum of the porphyrin metal complex, monoAP-Mn-DP-AP.

As the first embodiment of the present invention, the porphyrin metal complexes are used for DDS therapy capable of connecting with a physiologically active substance easily as missile therapy.

These porphyrin metal complexes are followings. The porphyrin metal complex represented by the formula (I), in which, 1) $R^1$ is —CH=CH$_2$ and $R^2$ is —CH(CH$_3$)—O—(CH$_2$)$_n$—NH$_2$ (wherein, n is the integer 2 or 3);
2) $R^1$ is —CH(CH$_3$)—O—(CH$_2$)$_n$—NH$_2$ (wherein, n is the integer 2 or 3) and $R^2$ is —CH=CH$_2$;
3) $R^1$ is —CH(CH$_3$)—OH and $R^2$ is —CH(CH$_3$)—O—(CH$_2$)$_n$—NH$_2$ (wherein, n is the integer 2 or 3);
4) $R^1$ is —CH(CH$_3$)—O—(CH$_2$)$_n$—NH$_2$ (wherein, n is the integer 2 or 3) and $R^2$ is —CH(CH$_3$)—OH;
5) both of $R^1$ and $R^2$ are —CH(CH$_3$)—O—(CH$_2$)$_n$—NH$_2$ (wherein, n is the integer 2 or 3); and the transition metal M is manganese (Mn).

Accordingly, first embodiment of the porphyrin complex of the present invention has the functional aminoalkoxy group at the side chain of the porphyrin ring. Therefore, the physiologically active compound having the acidic functional group such as carboxylic group, isothiocyanate group or azide group can be connected with the functional amino group of the porphyrin complex.

As the second embodiment of the present invention, the porphyrin metal complexes having nitroimidazole at the side chain thereof or a pharmaceutically acceptable salt thereof are followings. That is, the porphyrin metal complex represented by the formula (I), in which, $R^3$ is hydrogen atom or the group: —CO—(CH$_2$)$_m$—COOH; and 1) $R^1$ is —CH=CH$_2$ and $R^2$ is —CH(CH$_3$)O—(CH$_2$)$_n$—NH—$R^a$;
2) $R^1$ is —CH(CH$_3$)O—(CH$_2$)$_n$—NH—$R^a$ and $R^2$ is —CH=CH$_2$;
3) $R^1$ is —CH(CH$_3$)—OH and $R^2$ is —CH(CH$_3$)—O—(CH$_2$)$_n$—NH—$R^a$;
4) $R^1$ is —CH(CH$_3$)—O—(CH$_2$)$_n$—NH—$R^a$ and $R^2$ is —CH(CH$_3$)—OH;
5) both of $R^1$ and $R^2$ are —CH(CH$_3$)—O—(CH$_2$)$_n$—NH—$R^a$;

(wherein $R^a$ is the group represented by the following formula:

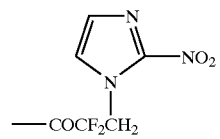

and the transition metal M is manganese (Mn), or a pharmaceutically acceptable salt thereof.

Accordingly, second embodiment of the porphyrin metal complex of the present invention is the one having nitroimidazole at the side chain of the porphyrin ring and ester. Such nitroimidazole derivative is connected to the functional amino group of the side chained aminoalkoxy group of porphyrin ring with carboxylic group of nitroimidazole derivative by the covalent bonding.

The porphyrin complexes having nitroimidazole represented by formula (I) are novel and can be prepared by the method mentioned below.

Firstly, a protoporphyrin dimethyl ester is converted into its HBr adduct compound, and the resulting HBr adduct compound is further converted into the compound having an aminoalkoxy group at the side chain of porphyrin ring by treating with the aminoalcohol compounds [Step (a)], and then, the resulting compound obtained in the Step (a) is treated with the transition metal such as manganese to obtain the porphyrin metal complex having a functional amino group at the terminal of the side chain of the porphyrin ring of the first embodiment of the present invention [Step (b)]. This functional amino group is capable of connecting with nitroimidazole derivatives easily.

It is not essential to conduct the reactions in the sequential order.

Then, the resulting porphyrin metal complex having a functional amino group at the terminal of the side chain of the porphyrin ring is reacted with the nitroimidazole derivative to obtain the porphyrin metal complex having nitroimidazole at the side chain of the porphyrin ring by amidation reaction between functional amino group and carboxylic group of the nitroimidazole derivative in Step (c). Finally, by esterified reaction of the resulting complex obtained in the Step (c) with acid anhydride such as succinic anhydride, the ester of the porphyrin metal complex having nitroimidazole at the side chain of the porphyrin ring, of the second embodiment of the present invention, is obtained [Step (d)].

Each of the steps is explained in more detail in the following.

Step (a) for conversion of the starting compound into a porphyrin compound having an aminoalkoxy group at the side chain of porphyrin ring can be conducted according to any of the conventional methods, such as methods disclosed in J. E. Falk: "Porphyrins and Metalloporphyrins" published by Elsevier in 1975; D. Dolphin: "The Porphyrins" published by Academic Press in 1978 and so on.

That is, in the Step (a), a protoporphyrin dimethyl ester can be converted into its HBr adduct compound in accordance with the patented method (Japanese Patent Application Laid-open No. 1-146615; corresponding to Japanese Patent No. 2,520,735) discovered by the present inventors. Then, the resulting HBr adduct compound is condensed with aminoalcohols having appropriate carbon atoms to obtain the porphyrin compound having an aminoalkyloxy group at the side chain of porphyrin ring. The aminoalcohols to be used in this reaction may include aminoethanol, aminopropanol and so on.

Next in the Step (b), the porphyrin compound having an aminoalkyloxy group at the side chain of porphyrin ring obtained in the Step (a) can be converted to its metal complex by reaction with the transition metal such as manganese (Mn) and cupper (Cu) to obtain the porphyrin metal complex having a functional amino group at the terminal of the side chain of the porphyrin ring, which is capable of easily connecting with nitroimidazole derivatives, of the first embodiment of the present invention.

The preferable porphyrin metal complex thus obtained is the porphyrin metal complex (hereinafter referred to as "diAP-Mn-DP-AP") represented by the following formula (I-a):

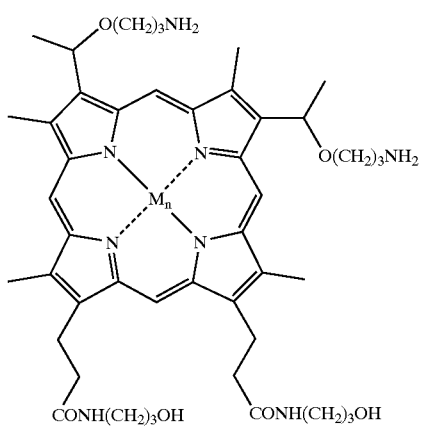

The reactivity of the functional amino group at the side chain of the porphyrin metal complex thus obtained was examined by the reaction with N-(tert-butoxycarbonyl) glycine (Boc-Gly) and diethylenetriaminepentaacetic dianhydride (DTPA dianhydride). This porphyrin metal complex can be easily amidated with these compounds. Furthermore, when the porphyrin metal complex was examined by dancyl methionine test, in which one of the present inventors has found a certain rule, it was confirmed that the porphyrin metal complex shows an excellent transferability to cancerous tissues and a strong photosensitivity.

Dancyl methionine test, a convenient test method for evaluating the strength of the photoreactivity by thin layer chromatography (TLC) or high performance liquid chromatography (HPLC) (see Japanese Patent Application Laid-open No. 5-97857), is also confirmed that the porphyrin metal complex of the present invention shows no phototoxicity.

Next, in the Step (c), the porphyrin metal complex having nitroimidazole at the side chain of porphyrin ring of the second embodiment of the present invention can be obtained from the porphyrin metal complex having the functional amino group at the side chain of the porphyrin ring by reacting with methyl 3-(2'-nitroimidazole) -2,2-difluoropropionate. The reaction can be conducted in the organic solvent such as methanol and ethanol under the presence of an appropriate week base such as triethylamine or dicyclohexcylamine under stirring.

Esterified process of the Step (d) can be conducted by the conventional manner used in the common organic synthesis technique. For example, the porphyrin metal complex having nitroimidazole at the side chain of the porphyrin ring obtained in the Step (c) is treated with succinic anhydride in the basic solvent such as pyridine to give the ester of porphyrin metal complex of the second embodiment of the present invention.

The preferable porphyrin metal complex thus obtained is the porphyrin metal complex having nitroimidazole at the side chain of the porphyrin ring (hereinafter referred to as "NI-AP-Mn-DP-AP-SUC") represented by the following formula (I-b):

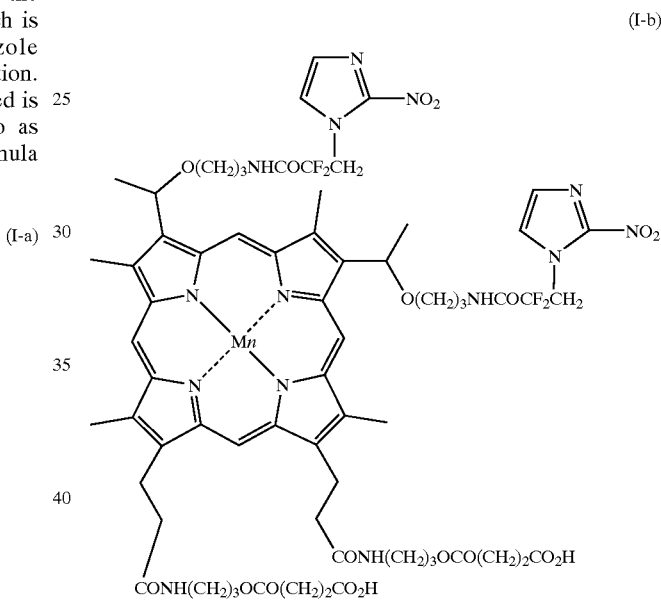

A pharmaceutical preparation comprising the porphyrin metal complex of formula (I) of the present invention may be prepared by per se conventional procedure, such as by simply dissolving the porphyrin metal complex in a suitable buffer solution. For the suitable additives, a pharmaceutically acceptable solubilizing agent (e.g., an organic solvent), a pH adjusting agent (e.g., hydrochloric acid, buffer solution), a stabilizer (e.g., ascorbic acid), excipient (e.g., glucose) or an isotonic agent (e.g., sodium chloride) can be further added.

The pharmaceutical preparation of the present invention as a contrast medium and a sensitizer used for diagnosis and/or treatment of cancer in MRI and/or radiotherapy has satisfactory properties such as a long phosphorescence life time, a good affinity to alubmine, a specific accumulability to a particular organ, especially to a cancer locus, a good cell killing effect, a good water solubility and purity. The good water solubility of the porphyrin metal complex enables preparation of a high concentration solution (e.g., 30 mg/ml), and furthermore, the porphyrin metal complex exhibits a high stability in vivo.

The porphyrin metal complex of the first embodiment of the present invention is structurally characterized in that it has the functional amino group at the side chain of the porphyrin ring, and the transition metal in the porphyrin skeleton thereof. As the result, the porphyrin metal complex may connect with various physiologically active compounds having the functional acidic group by covalent bonding and exhibits various biochemical properties for DDS therapy without any phototoxicity. Therefore, first embodiment of the porphyrin metal complex of the present invention is highly useful as a carrier of the DDS therapy for the specific organ, especially cancer locus, malignant tumor as well as neovascularization.

On the contrary, the porphyrin metal complex having nitroimidazole at the side chain of the porphyrin ring as the second embodiment of the present invention is structurally characterized in that it has imidazole substituent at the terminal of the side chain of the porphyrin skeleton via the functional amino group, and the transition metal in the porphyrin skeleton thereof. As the result, the porphyrin metal complex exhibits various physiological and pharmacological properties. That is, the porphyrin complex of the present invention selectively accumulates in tumor cells and is excreted therefrom at a slow rate. On the other hand, excretion from normal organs and cells is rapid. Although, most porphyrin derivatives basically exhibit phototoxiciy, the porphyrin metal complex of the present invention is designed to inhibit such phototoxiciy. In addition, the porphyrin metal complex of the present invention is designed to connect with a physiologically active compound such as nitroimidazole for radiosensitizer, and to diagnose and/or treat the cancer.

EXAMPLES

The present invention will be described in more detail by referring to the following examples, but it is to be noted that the present invention is not limited by these Examples in any way.

Example 1

Reaction of Protoporphyrin Dimethylester with HBr

According to the method described in Japanese Patent Application Laid-open No. 1-146615, to a suspension of 50 g of protoporphyrin dimethylester [PP-Me] in 170 ml of acetic acid was added 340 ml of a mixture solution of 30% HBr/acetic acid. Then, the reaction mixture solution was left for 2 days for completion of the reaction. After the reaction, the solvent was concentrated under reduced pressure to give about 50 g of HBr adduct product of PP-Me (Br-DP) from the residue.

Example 2

Aminopropoxylation Reaction of Br-DP 350 ml of aminopropylalcohol hydrochloride was added to 50 g of Br-DP obtained by the Example 1 above, and the reaction mixture was stirred for about 1 month at 55° C. After the completion of the reaction (confirming by TLC), water was added to this reaction mixture, and then, pH of the reaction mixture was adjusted to 10.5 by adding 20% sodium hydroxide aqueous solution and the hydrolysis reaction was conducted. After the resulting precipitate was allowed to stand for 30 minutes, then the pH of the solution was adjusted to 3.0 by adding 10% hydrochloride aqueous solution. The solution was adsorbed on synthetic adsorbent (HP-20), and the adsorbent was eluted by methanol to give 32.5 g of amimopropoxyporphyrin compound (AP-DP-AP).

Example 3

Metal Complex Reaction of AP-DP-AP by Manganese 32.5 g of AP-DP-AP obtained in the Example 2 above was dissolved in 975 ml of methanol and to this solution was added methanol solution of manganese (II) acetate tetrahydrate (32.5 g/163 ml) and then the mixture was stirred for 3 hours under stirring. After confirming the completion of the reaction by TLC, the reaction mixture was condensed to about half volume under reduced pressure to give the crude product of aminopropoxyporphyrin manganese complex (AP-Mn-DP-AP) as muddy substance.

Example 4

Separation and Purification of Monoaminopropoxyporphyrin Manganese Complex (monoAP-Mn-DP-AP) and Diaminopropoxy-Porphyrin Manganese Complex (diAP-Mn-DP-AP) by Column Chromatography The crude product of aminopropoxyporphyrin manganese complex (AP-Mn-DP-AP) obtained in the Example 3 above was subjected to silica gel column chromatography and eluted with ethyl acetate, ethyl acetate/methanol (1:1), methanol and methanol/acetic acid (20:1), respectively. Monoaminopropoxyporphyrin manganese complex (monoAP-Mn-DP-AP) was isolated from the eluted part by methanol and then diaminopropoxyporphyrin manganese complex (diAP-Mn-DP-AP) was also isolated from the eluted part by methanol/acetic acid.

Figure 2:
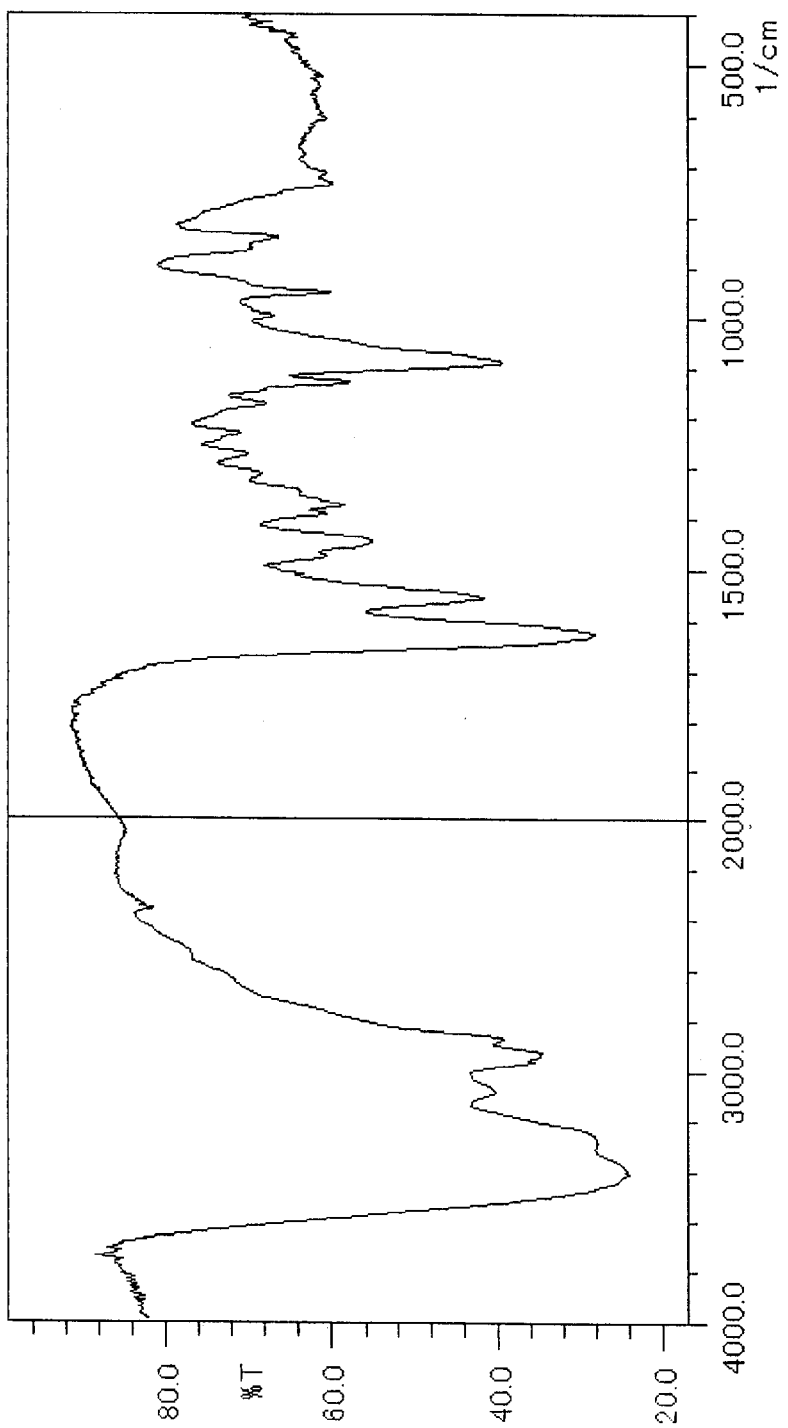
FIG. 2 shows an infrared absorption spectrum of the porphyrin metal complex, diAP-Mn-DP-AP.

The physiological properties of these products are as follow.
(1) monoAP-Mn-DP-AP
  Mass spectrum: M$^+$ 804 ($C_{43}H_{55}N_7O_5Mn$)
  The infrared absorption spectrum of monoAP-Mn-DP-AP is shown in FIG. 1.
(2) diAP-Mn-DP-AP
  Mass spectrum: M$^+$ 879 ($C_{46}H_{64}N_8O_6Mn$)
  The infrared absorption spectrum of monoAP-Mn-DP-AP is shown in FIG. 2.

Example 5

Confirmation of the Presence of the Functional Amino Group by Reaction with Boc-Gly The following experiments were conducted to confirm the presence of the terminal functional amino group of monoAP-Mn-DP-AP and diAP-Mn-DP-AP obtained by the Example 4 above.

Each of monoAP-Mn-DP-AP and diAP-Mn-DP-AP obtained by the Example 4 was separately weighed out (100 mg each) and dissolved in dimethylformamide respectively. To the resultant solution was added 100 mg of N-(tert-butoxycarbonyl)glycine (Boc-Gly), and then, 100 mg of water soluble carbodiimide (WSC) was added gradually over 30 minutes to the reaction mixture under stirring. After the reaction, protection of the amino group was confirmed by silica gel TLC plate [eluent: n-butanol/water/acetic acid (4:5:1)]. That is, Rf of monoAP-Mn-DP-AP (0.14) was disappeared and 0.8 of Rf value was newly appeared by protection of the amino group. Also, Rf of diAP-Mn-DP-AP (0.26) was disappeared and 0.8 of Rf value was newly appeared by protection of the amino group.

Then, water was added to the each reaction mixture and the resulting precipitate was collected by filtration and washed with water to give 70 mg of monoBoc-Gly-monoAP-Mn-DP-AP, which is Boc-Gly introduced product of monoAP-Mn-DP-AP, and 80 mg of diBoc-Gly-diAP-Mn-DP-AP, which is Boc-Gly introduced product of diAP-Mn-DP-AP, respectively.

Although, each obtained Boc-Gly introduced product of monoAP-Mn-DP-AP and Boc-Gly introduced product of diAP-Mn-DP-AP was subjected to alkali hydrolyze by the conventional manner, no changes on the TLC plate were observed. Accordingly, it was confirmed that monoAP-Mn-DP-AP and diAP-Mn-DP-AP has the terminal functional amino group respectively.

The presence of the terminal amino group was also confirmed by acetylation and diethylenetriaminepentaacetylation (DTPA) other than N-(tert-butoxy)glycination (Boc-Glycine).

Therefore, the porphyrin compound represented by the formula (I) of the present invention has a functional (reactive) terminal amino group at the side chain of porphyrin.

Example 6

Amidation Reaction with Nitroimidazole 1 g of diAP-Mn-DP-AP was dissolved in 10 ml of methanol, and to this solution was added 1 ml of dicyclohexyl amine (DCHA) and methanol solution of 1 g of methyl 3-(2'-nitroimidazole)-2,2-difluoro-propionate in 1 ml of methanol and then, the reaction mixture was stirred for 2 hours under stirring. After the reaction, the reaction solution was adsorbed on synthetic adsorbent (HP-20), and the adsorbent was washed with water and eluted by methanol to give 1 g of porphyrin having nitroimidazole at the side chain of the porphyrin ring (NI-diAP-Mn-DP-AP).

Example 7

Esterified Reaction with Succinic Anhydride 1 g of NI-diAP-Mn-DP-AP was dissolved in 10 ml of pyridine and to this solution was added the 1 g of succinic anhydride, then the reaction mixture was stirred for 4 hours. After the reaction, mixture was absorbed to synthetic adsorbent (HP-20), and the adsorbent was washed with water and eluted by methanol to give 1 g of succinic ester of the porphyrin having nitroimidazole at the side chain of the porphyrinre ring (NI-diAP-Mn-DP-AP-SUC).

Figure 3:
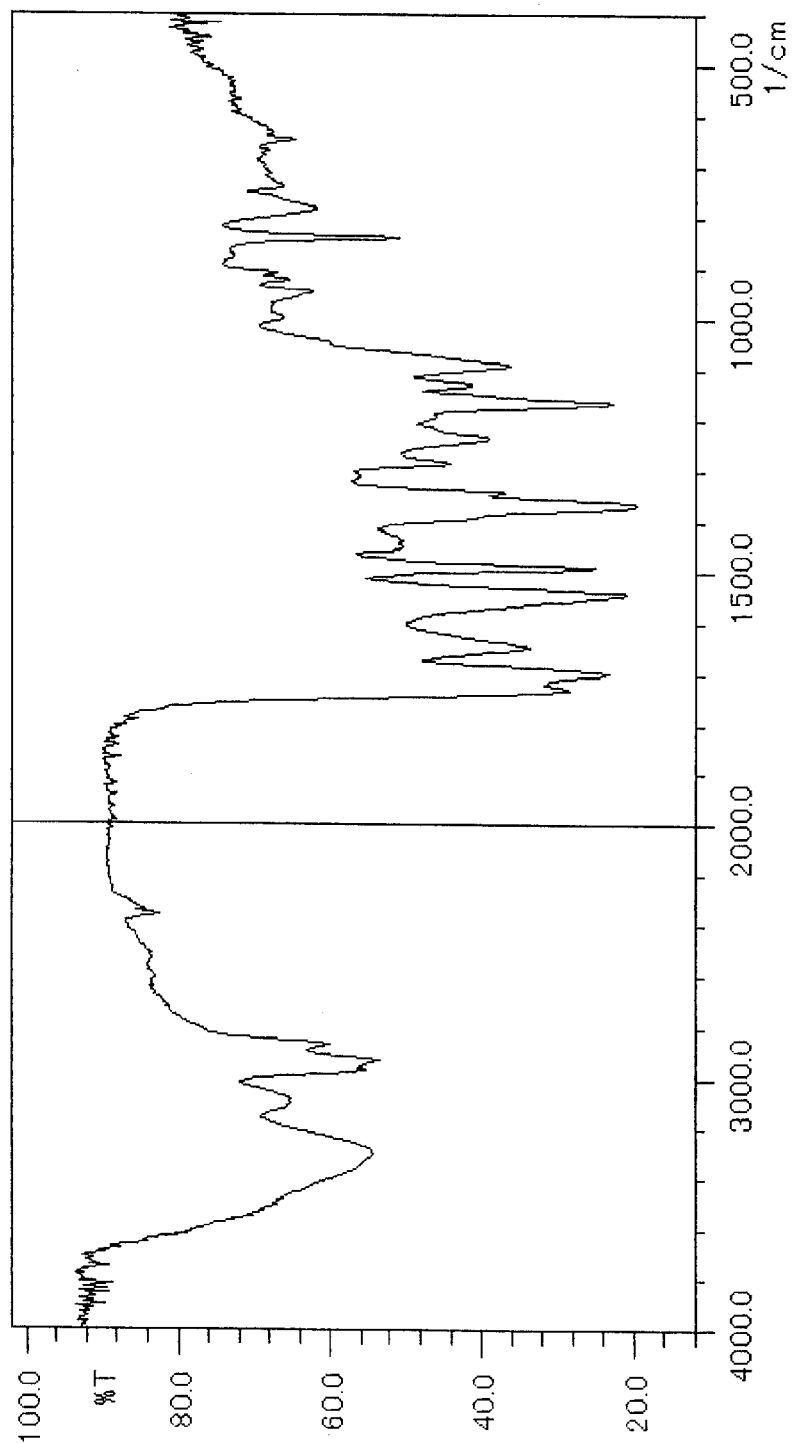
FIG. 3 shows an infrared absorption spectrum of succinate of diaminopropoxyporphyrin manganese complex having nitorimidazole, NI-diAP-Mn-DP-AP-SUC.

The infrared absorption spectrum of monoAP-Mn-DP-AP is shown in FIG. 3.

Maleic ester of the porphyrin having nitroimidazole at the side chain of the porphyrinre ring was also obtained by using maleic anhydride instead of succinic anhydride.

Example 8

Effects on the Radiotherapy

NI-diAP-Mn-DP-AP-SUC in phosphate buffer solution was intraperitoneal administered (100 mg/kg) to C3H/He mice (5 mice/group), which were transplanted SCCVII tumor cells 14 to 21 days before administration, then irradiated with 60 Gly radio ray and measured the volume of cancer.

The measurements were made at 1 to 13 days after the administration. The results were shown in FIG. 4. In the figure, the volume of cancer before administration is defined to 1 as the standard.

Figure 4:
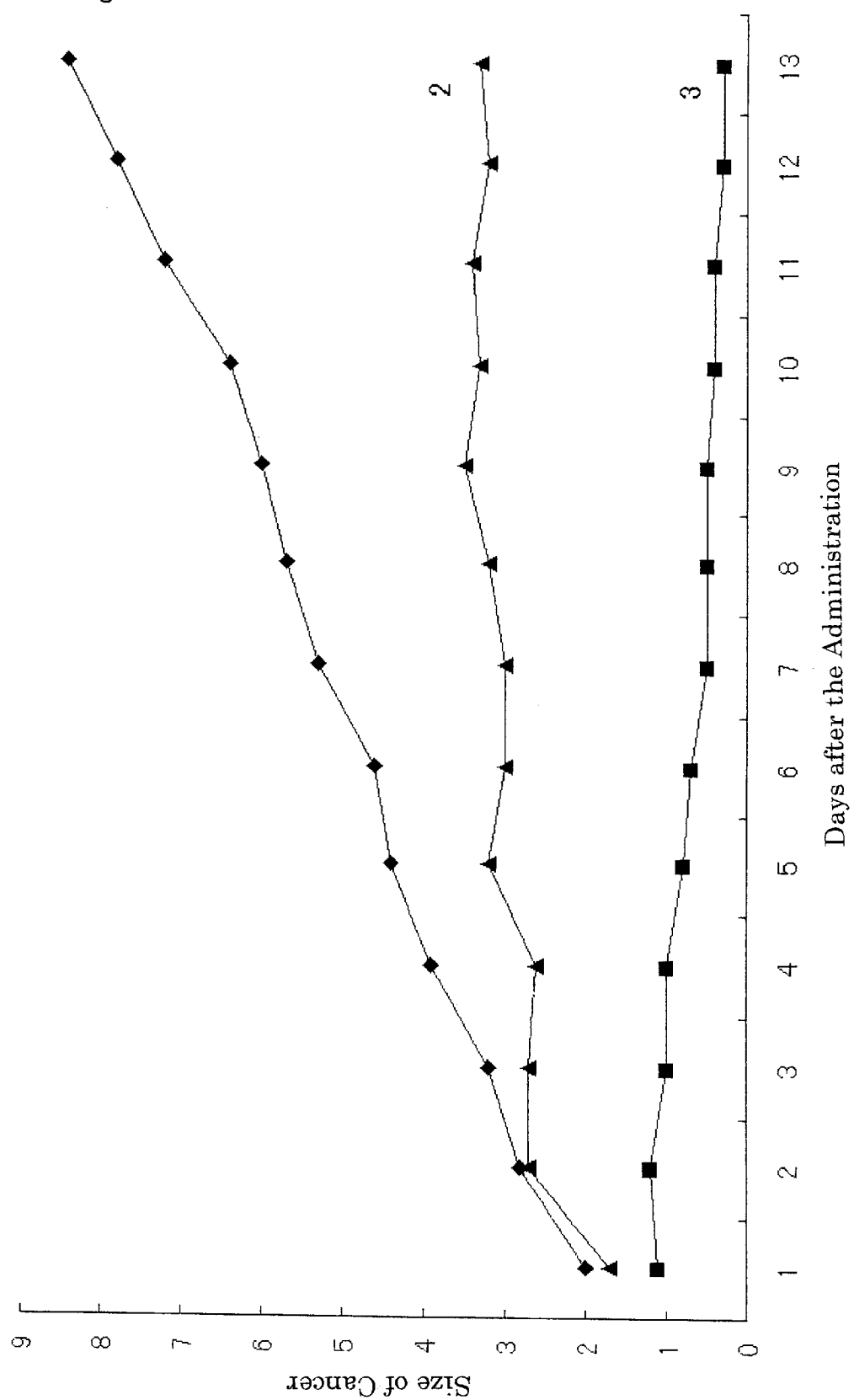
FIG. 4 shows the growth of cancer in the relative volume ratio from the initial day treated with succinate of diaminopropoxyporphyrin mangan complex having nitorimidazole (NI-diAP-Mn-DP-AP-SUC). In the graphic, the curve No. 1 represents the result of the group not treated, the curve No. 2 represents the results of the group treated with radiotherapy alone, and the curve No. 3 represents the result of the group treated with radiotherapy and NI-diAP-Mn-DP-AP-SUC.

As shown from the results in FIG. 4, it was confirmed the radiosensitizer effect of NI-diAP-Mn-DP-AP-SUC.

Example 9

MRI Imaging Effect

NI-diAP-Mn-DP-AP-SUC in phosphate buffer solution was intravenously administered (100 mg/kg) to C3H/He mice, which were transplanted SCCVII tumor cells 14 to 21 days before the administration. 1 hour after the administration, MRI imaging was conducted.

Figure 5:
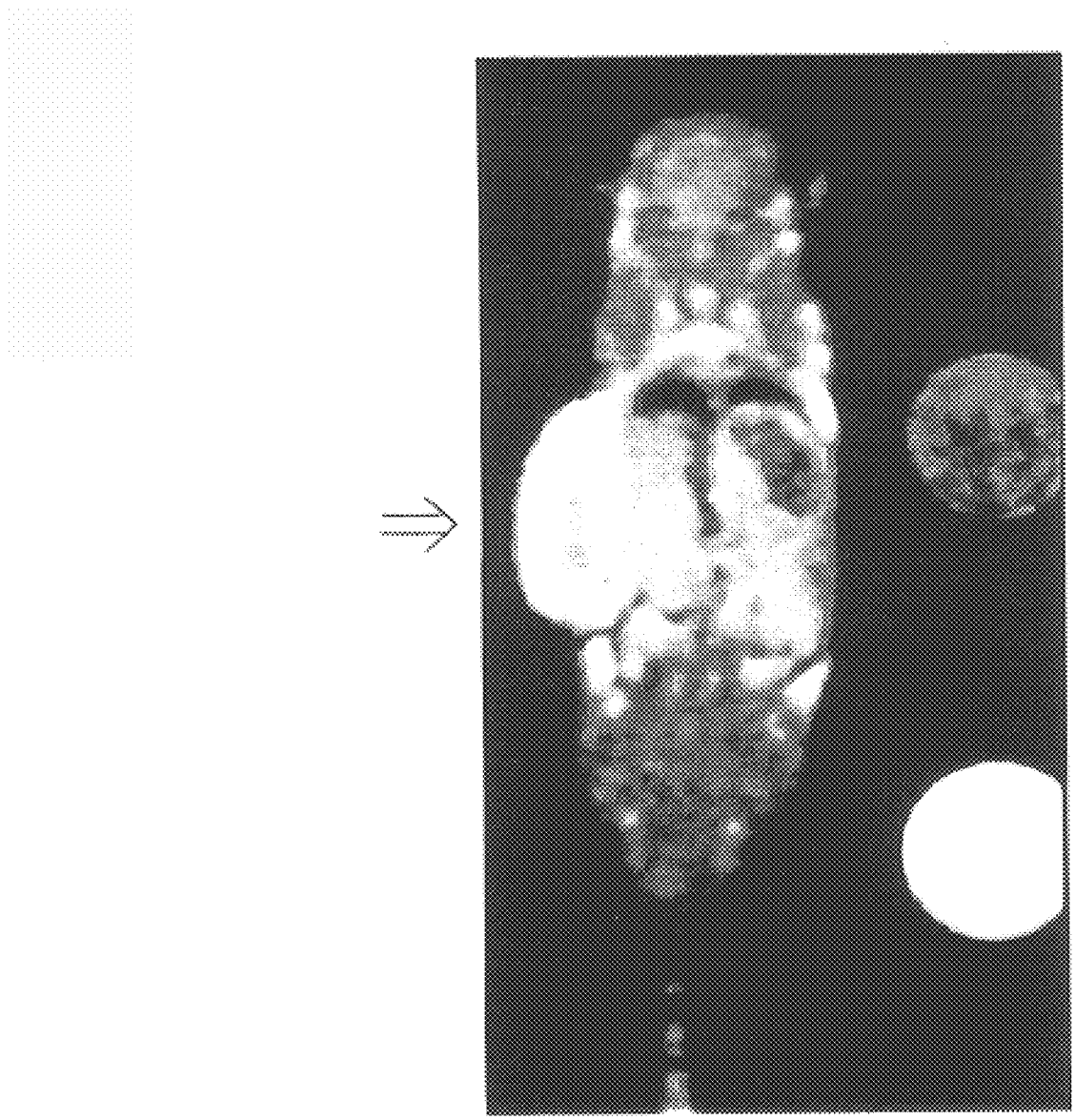
FIG. 5 shows the MRI image of mice after 1 hour from the treatment with succinate of diaminopropoxyporphyrin mangan complex having nitorimidazole (NI-diAP-Mn-DP-AP-SUC). In the figure, the arrow shows the position of tumor.

Resulting MRI image was shown in FIG. 5.

As shown from FIG. 5, it was confirmed that the clearly MRI imaging picture of tumor was obtained due to the use of the porphyrin metal complex of the present invention.

INDUSTRIAL APPLICABILITY

The porphyrin metal complex having nitroimidazole of the present invention is the porphyrin manganese complex in which nitroimidazole is connected with the reactive amino group at the side chain of the porphyrin ring. Therefore, this compound exhibits the property as a contrast medium used for diagnosis in magnetic resonance imaging (MRI) therapy. Further, this compound also exhibits the property as therapeutic agent in radiotherapy of cancer due to the radiosensitizing effect of nitroimidazole type drug. Therefore, the porphyrin metal complex having nitroimidazole of the present invention is extremely useful compound for diagnosis and/or treatment of cancer.

Furthermore, the porphyrin compound of another embodiment of the present invention is structurally characterized in that it has the functional amino group at the side chain of the porphyrin ring. Therefore, various physiologically active compounds having the functional acidic group such as anticancer agent can easily connect with said porphyrin compound. Additionally, said porphyrin compound shows no phototoxicity and therefore, is extremely useful compound as a carrier of the medicines in DDS therapy.

What is claimed is:

1. A porphyrin metal complex represented by the following formula (I):

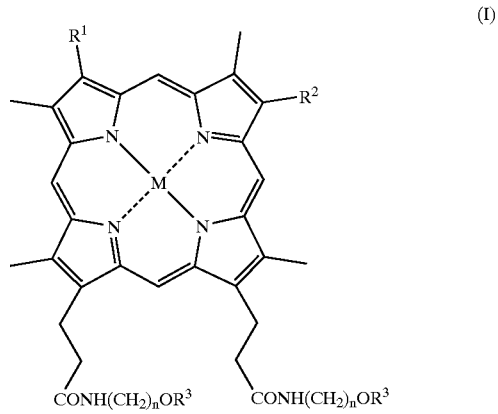

[wherein,
when one of $R^1$ and $R^2$ is —CH=$CH_2$ or —CH($CH_3$)—OH, the other is —CH($CH_3$)—O—$(CH_2)_n$—NH—$R^a$; or both of $R^1$ and $R^2$ are —CH($CH_3$)—O—$(CH_2)_n$—NH—$R^a$;
$R^3$ is hydrogen atom or —CO—$(CH_2)_m$—COOH;
M is transition metal of Mn, Fe, Co or Cu], in which, $R^a$ is hydrogen atom or the group represented by the following formula:

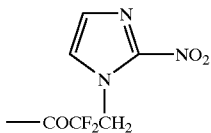

n and m are the integer 2 or 3,
or a pharmaceutically acceptable salt thereof.

2. The porphyrin metal complex of the formula (I) claimed in claim 1, wherein when one of $R^1$ and $R^2$ is —CH=CH$_2$ or —CH(CH$_3$)—OH, the other is —CH(CH$_3$)—O—(CH$_2$)$_n$—NH$_2$, or both of $R^1$ and $R^2$ are —CH(CH$_3$)—O—(CH$_2$)$_n$—NH$_2$; $R^3$ is hydrogen atom; n is the integer 2 or 3; and M is transition metal of Mn, Fe, Co or Cu.

3. The porphyrin metal complex claimed in claim 2, wherein when one of $R^1$ and $R^2$ is —CH=CH$_2$, the other is —CH(CH$_3$)—O—(CH$_2$)$_n$—NH$_2$ (in which n is the integer 2 or 3); n is the integer 2 or 3; and M is transition metal of Mn, Fe, Co or Cu.

4. The porphyrin metal complex claimed in claim 2, wherein when one of $R^1$ and $R^2$ is —CH(CH$_3$)—OH, the other is —CH(CH$_3$)—O—(CH$_2$)$_n$—NH$_2$ (in which n is the integer 2 or 3); n is the integer 2 or 3; and M is transition metal of Mn, Fe, Co or Cu.

5. The porphyrin metal complex claimed in claim 2, wherein both of $R^1$ and $R^2$ are —CH(CH$_3$)—O—(CH$_2$)$_n$—NH$_2$ (in which n is the integer 2 or 3).

6. The porphyrin metal complex claimed in any one of claims 1 to 5, wherein the transition metal is manganese (Mn).

7. The porphyrin metal complex having nitroimidazole in the molecule represented by the formula (I) claimed in claim 1, wherein,
when one of $R^1$ and $R^2$ is —CH=CH$_2$ or —CH(CH$_3$)—OH, the other is —CH(CH$_3$)—O—(CH$_2$)$_n$—NH—$R^a$; or both of $R^1$ and $R^2$ represent —CH(CH$_3$)—O—(CH$_2$)$_n$—NH—$R^a$;
$R^3$ is hydrogen atom or —CO—(CH$_2$)$_m$—COOH; and
M is transition metal of Mn, Fe, Co or Cu],
(in which, $R^a$ is the group represented by the following formula:

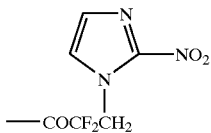

n and m are the integer 2 or 3),
or a pharmaceutically acceptable salt thereof.

8. The porphyrin metal complex having nitroimidazole in the molecule claimed in claim 7, wherein when one of $R^1$ and $R^2$ is —CH=CH$_2$, the other is —CH(CH$_3$)—O—(CH$_2$)$_n$—NH—$R^a$; $R^3$ is —CO—(CH$_2$)$_m$—COOH, or a pharmaceutically acceptable salt thereof.

9. The porphyrin metal complex having nitroimidazole in the molecule claimed in claim 7, wherein when one of $R^1$ and $R^2$ is —CH(CH$_3$)—OH, the other is —CH(CH$_3$)—O—(CH$_2$)$_n$—NH—$R^a$; $R^3$ is —CO—(CH$_2$)$_m$—COOH, or a pharmaceutically acceptable salt thereof.

10. The porphyrin metal complex having nitroimidazole in the molecule claimed in claim 7, wherein both of $R^1$ and $R^2$ are —CH(CH$_3$)—O—(CH$_2$)$_n$—NH—$R^a$; $R^3$ is —CO—(CH$_2$)$_m$—COOH, or a pharmaceutically acceptable salt thereof.

11. The porphyrin metal complex having nitroimidazole in the molecule claimed in claim 7, wherein n is 3; both of $R^1$ and $R^2$ are —CH(CH$_3$)—O—(CH$_2$)$_n$—$R^a$; and $R^3$ is —CO—(CH$_2$)$_3$—COOH, or a pharmaceutically acceptable salt thereof.

12. The porphyrin metal complex having nitroimidazole in the molecule claimed in claim 7, wherein when one of $R^1$ and $R^2$ is —CH=CH$_2$, the other is —CH(CH$_3$)—O—(CH$_2$)$_n$—NH—$R^a$; and $R^3$ is hydrogen atom, or a pharmaceutically acceptable salt thereof.

13. The porphyrin metal complex having nitroimidazole in the molecule claimed in claim 7, wherein when one of $R^1$ and $R^2$ is —CH(CH$_3$)—OH, the other is —CH(CH$_3$)—O—(CH$_2$)$_n$—NH—$R^a$; and $R^3$ is hydrogen atom, or a pharmaceutically acceptable salt thereof.

14. The porphyrin metal complex having nitroimidazole in the molecule claimed in claim 7, wherein both of $R^1$ and $R^2$ are —CH(CH$_3$)—O—(CH$_2$)$_n$—NH—$R^a$; and $R^3$ is hydrogen atom, or a pharmaceutically acceptable salt thereof.

15. The porphyrin metal complex having nitroimidazole in the molecule claimed in claim 7, wherein n is 3; both of $R^1$ and $R^2$ are —CH(CH$_3$)—O—(CH$_2$)$_n$—$R^a$; and $R^3$ is hydrogen atom, or a pharmaceutically acceptable salt thereof.

16. The porphyrin metal complex having nitroimidazole in the molecule claimed in any one of claims 7 to 15, wherein the transition metal is manganese (Mn), or a pharmaceutically acceptable salt thereof.

17. A contrast medium comprising the porphyrin metal complex having nitroimidazole in the molecule claimed in any one of claims 7 to 15, or a pharmaceutically acceptable salt thereof.

18. A contrast medium comprising the porphyrin metal complex having nitroimidazole in the molecule claimed in any one of claims 7 to 15, which is used for magnetic resonance imaging (MRI) therapy, or a pharmaceutically acceptable salt thereof.

19. A radiosensitizer comprising the porphyrin metal complex having nitroimidazole in the molecule claimed in any one of claims 7 to 15, or a pharmaceutically acceptable salt thereof.

20. A method for diagnosing cancer by administering the porphyrin metal complex having nitroimidazole in the molecule or a pharmaceutically acceptable salt thereof claimed in any one of claims 7 to 15, and using it as a contrast medium.

* * * * *